(12) United States Patent
Sim

(10) Patent No.: US 6,947,588 B2
(45) Date of Patent: Sep. 20, 2005

(54) EDGE NORMAL PROCESS

(75) Inventor: Hak Chuah Sim, Dallas, TX (US)

(73) Assignee: August Technology Corp., Bloomington, MN (US)

(*) Notice: Subject to any disclaimer, the term of this patent is extended or adjusted under 35 U.S.C. 154(b) by 0 days.

(21) Appl. No.: 10/890,692

(22) Filed: Jul. 14, 2004

(65) Prior Publication Data

US 2005/0013474 A1 Jan. 20, 2005

Related U.S. Application Data

(60) Provisional application No. 60/486,952, filed on Jul. 14, 2003.

(51) Int. Cl.$^7$ .......................... G06K 9/00; G01R 31/26
(52) U.S. Cl. ........................... 382/149; 438/14
(58) Field of Search ................. 382/144–145, 382/149, 266, 312; 356/237.1, 237.2, 237; 438/14, 582; 355/53

(56) References Cited

U.S. PATENT DOCUMENTS

| | | | |
|---|---|---|---|
| 4,328,553 A | 5/1982 | Fredriksen et al. | 356/139.04 |
| 4,464,705 A | 8/1984 | Horowitz | 362/12 |
| 4,644,172 A | 2/1987 | Sandland et al. | 250/548 |
| 4,823,394 A | 4/1989 | Berkin et al. | 382/145 |
| 5,091,963 A | 2/1992 | Litt et al. | 382/149 |
| 5,497,381 A | 3/1996 | O'Donoghue et al. | 714/745 |
| 5,592,295 A | 1/1997 | Stanton et al. | 356/426 |
| 5,640,200 A | 6/1997 | Michael | 348/87 |
| 5,641,960 A | 6/1997 | Okubo et al. | 250/310 |
| 5,787,190 A | 7/1998 | Peng et al. | 382/145 |
| 5,822,055 A | 10/1998 | Tsai et al. | 356/237.1 |
| 5,850,466 A | 12/1998 | Schott | 382/141 |
| 5,854,674 A * | 12/1998 | Lin | 356/237.1 |
| 5,856,844 A | 1/1999 | Batterman et al. | 348/207.99 |
| 5,859,698 A * | 1/1999 | Chau et al. | 356/237.2 |
| 5,917,588 A | 6/1999 | Addiego | 356/237.1 |
| 5,949,901 A | 9/1999 | Nichani et al. | 382/149 |
| 6,067,163 A * | 5/2000 | Guldi et al. | 356/394 |
| 6,137,303 A | 10/2000 | Deckert et al. | 324/765 |
| 6,140,254 A | 10/2000 | Endisch et al. | 438/787 |
| 6,147,357 A | 11/2000 | Nicolescu | 250/559.46 |
| 6,153,361 A | 11/2000 | Liu et al. | 430/331 |
| 6,314,379 B1 | 11/2001 | Hu et al. | 702/81 |
| 6,324,298 B1 | 11/2001 | O'Dell et al. | 382/149 |
| 6,412,326 B1 | 7/2002 | Hubbard et al. | 73/1.01 |
| 6,432,800 B2 * | 8/2002 | Park | 438/582 |
| 6,565,920 B1 | 5/2003 | Endisch | 427/240 |
| 6,640,151 B1 | 10/2003 | Somekh et al. | 700/121 |
| 6,708,074 B1 | 3/2004 | Chi et al. | 700/121 |
| 2003/0030050 A1 | 2/2003 | Choi | |
| 2003/0202178 A1 | 10/2003 | Tsuji et al. | |

* cited by examiner

Primary Examiner—Kanjishai Patel
(74) Attorney, Agent, or Firm—Dicke, Billig & Czaja, PLLC

(57) ABSTRACT

An edge inspection method for detecting defects on a wafer edge normal surface includes acquiring a set of digital images which captures a circumference of the wafer. An edge of the wafer about the circumference is determined. Each digital image is segmented into a plurality of horizontal bands. Adjacent edge clusters about the circumference of the wafer are combined into edge pixel bins. The edge pixel bins are analyzed via edge clusters analysis to identify defects. The edge pixel bins are also analyzed via blob analysis to determine defects.

32 Claims, 13 Drawing Sheets

(a) Raw local bands lateral intensity variation (b) Global lateral intensity variation (c) Local bands lateral intensity variation

EDGE NORMAL PROCESS

CROSS-REFERENCE TO RELATED APPLICATIONS

This application claims the benefit priority under 35 U.S.C. §119(e) to U.S. Provisional Application Ser. No. 60/486,952, filed Jul. 14, 2003 and entitled "EDGE NORMAL PROCESS".

BACKGROUND

1. Technical Field

The present invention relates to an inspection system that inspects the edge normal surface of a semiconductor wafer or like substrate such as a microelectronics substrate to identify defects therealong.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics. Therefore, there is a need for faster, more advanced computers and electronics. To satisfy this need, quality and efficiency is required, whether it be on an assembly line, on test equipment in a lab, on the personal computer at one's desk, or in home electronics and toys.

Manufacturers of semiconductors have made vast improvements in end product quality, speed and performance as well as in manufacturing process quality, speed and performance. However, there continues to be demand for faster, more reliable and higher performing semiconductors. To assist these demands, better inspection is necessary to increase yields. One area that has been generally ignored is the edge of the semiconductor wafer. It is believed that inspection of such edge area will lead to better information on defects, thereby enabling improved process control and improved wafer yields.

In the past when attempts to inspect the edge of a semiconductor wafer were made, it was generally performed manually with the naked eye of a human operator. As with all human inspection, repeatability, training, and capture rate are subject to flux. It has recently been discovered that edge inspection is important for detecting delamination of thin films, chipping and cracking of the wafer, resist removal metrology, and particle detection that all cause yield issues in a modern fab. Furthermore, the edge of the wafer is a leading indicator of process status, and by monitoring the edge of the wafer for changes in appearance, tighter process control can be implemented.

One proposed solution looks directly at the edge normal of the wafer. This solution provides limited benefits in detecting particles and chip-outs, and is limited in classifying defects. There is a need for continued improvement in edge inspection, in particular, for unique, robust methods, processes, and algorithms to accomplish an edge normal inspection.

SUMMARY

An edge inspection method for detecting defects on a wafer edge normal surface includes acquiring a set of digital images which captures a circumference of the wafer. An edge of the wafer about the circumference is determined. Each digital image is segmented into a plurality of horizontal bands. Adjacent edge clusters about the circumference of the wafer are combined into edge pixel bins. The edge pixel bins are analyzed via edge clusters analysis to identify defects. The edge pixel bins are also analyzed via blob analysis to determine defects.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION

The edge normal inspection method of the present invention may be used on any of a number of edge inspection systems. The present invention is a method of detecting defects along the wafer edge normal surface. In general, the method of finding defects on the wafer edge normal of the present invention involves the following steps: (1) detection of the wafer edge, (2) image normalization, (3) horizontal band segmentation, (4) lateral illumination correction, (5) creation of a dynamic reference image, (6) image edge analysis, (7) edge pixels bin clustering, (8) edge cluster analysis, (9) blob analysis on difference image, and (10) statistical manipulation.

Figure 1:
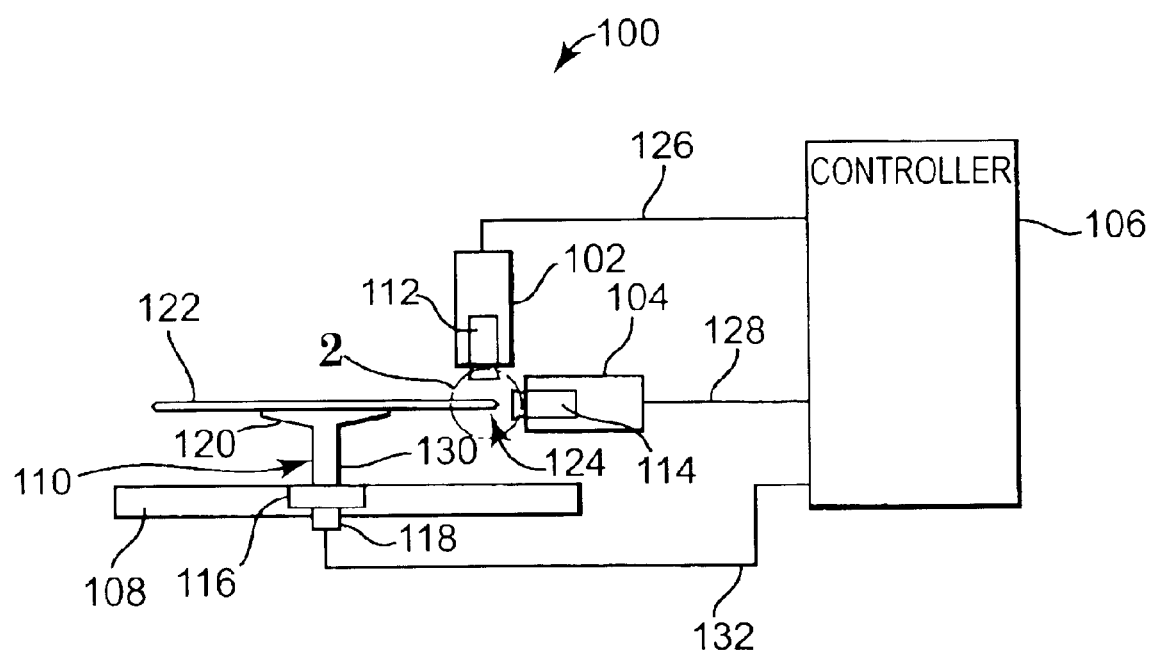
FIG. 1 is a schematic diagram illustrating one embodiment of an edge inspection system.

FIG. 1 is a schematic diagram illustrating one embodiment of an edge inspection system 100. Edge inspection system 100 includes an edge top sensor 102, an edge normal sensor 104, a controller 106, a base 108, and a stage 110. Top edge sensor 102 includes a camera 112, and normal edge sensor 104 includes a camera 114. Stage 110 includes a motor 116, an encoder 118, and a support plate 120. Motor 116 is coupled to encoder 118 and support plate 120 to rotate support plate 120. Encoder 118 provides counts for controlling the position of motor 116. Support plate 120 supports a wafer 122 for inspecting an edge 124 of wafer 122. Controller 106 is electrically coupled to top edge sensor 102 through communication link 126, normal edge sensor 104 through communication link 128, and staging 130 through communication link 132. Controller 106 controls edge top sensor 102, edge normal sensor 104, and staging 130 for inspecting edge 124 of wafer 122.

Figure 2:
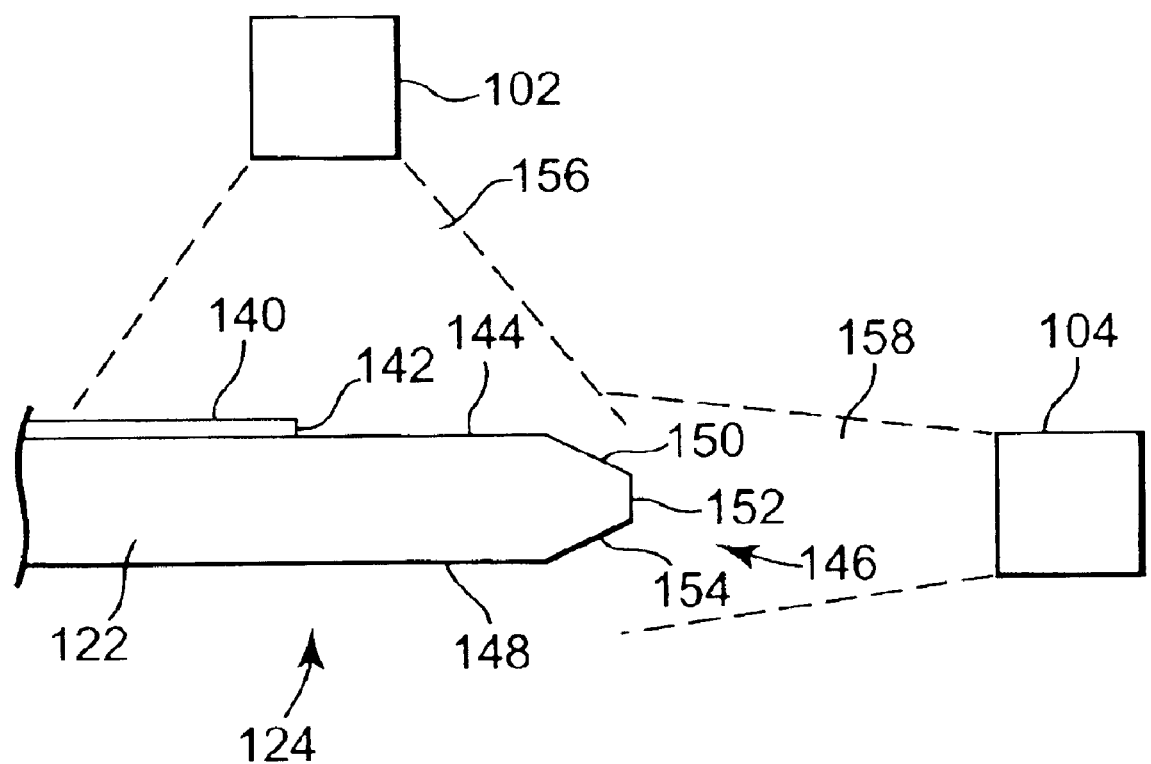
FIG. 2 is a schematic diagram illustrating the indicated portion of the edge inspection system illustrated in FIG. 1 in more detail.

FIG. 2 is a schematic diagram illustrating the indicated portion of edge inspection system 100 illustrated in FIG. 1 in more detail. FIG. 2 illustrates edge top sensor 102, normal edge sensor 104, and edge 124 of wafer 122. Edge 124 of wafer 122 includes resist layer 140 having an edge bead removal (EBR) line 142, edge exclusion region 144, wafer edge bevel 146, and wafer bottom 148. Wafer edge bevel 146 includes top bevel 150, wafer edge normal 152, and bottom bevel 154. Edge top sensor 102 has a field of view as indicated at 156. Edge normal sensor 104 has a field of view as indicated at 158. Edge inspection system 100 inspects and/or measures along edge 124 of wafer 122 including resist layer 140, edge exclusion region 144, top bevel 150, wafer edge normal 152, and bottom bevel 154.

Figure 3:
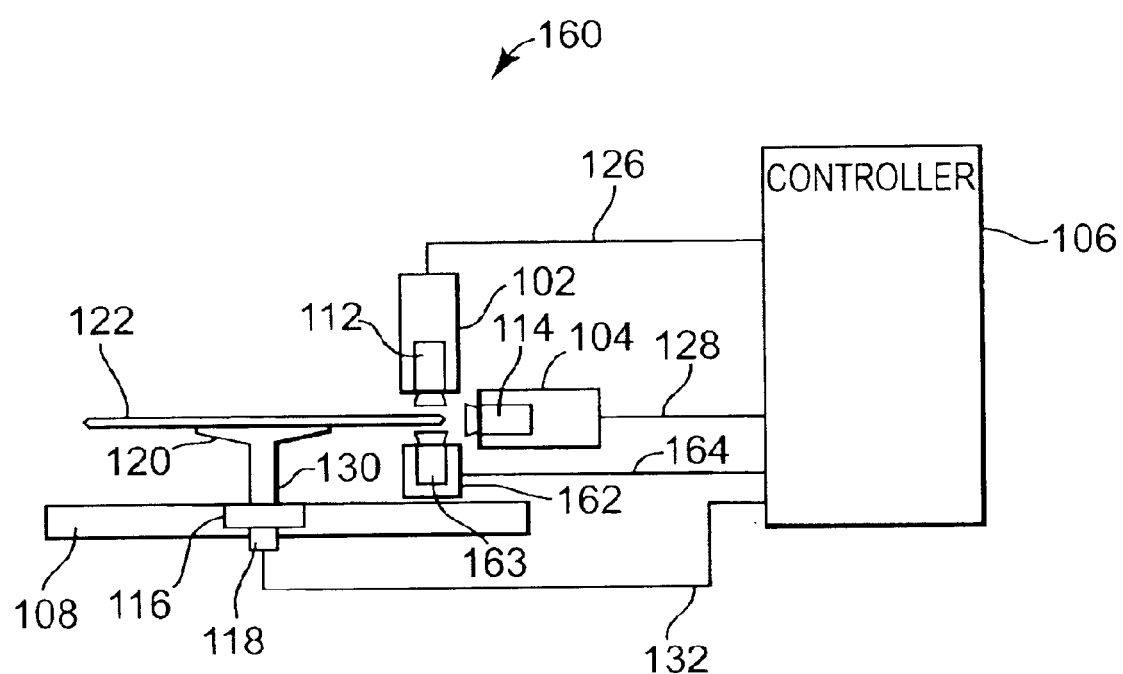
FIG. 3 is a schematic diagram illustrating another embodiment of an edge inspection system.

FIG. 3 is a schematic diagram illustrating an alternative embodiment of an edge inspection system 160. Edge inspection system 160, in addition to edge top sensor 102, edge normal sensor 104, controller 106, staging 130, and base 108, includes edge bottom sensor 162, camera 163, and communication link 164.

In this embodiment, both the top and bottom edge of wafer 122 are inspected. Edge inspection system 160 performs edge inspection in substantially the same manner as edge inspection system 100 (FIG. 1), except that edge inspection system 160 inspects both the top of edge 124 (FIG. 2) and the bottom of edge 124 of wafer 106 via edge bottom sensor 162, camera 163, and communication link 164.

Figure 4:
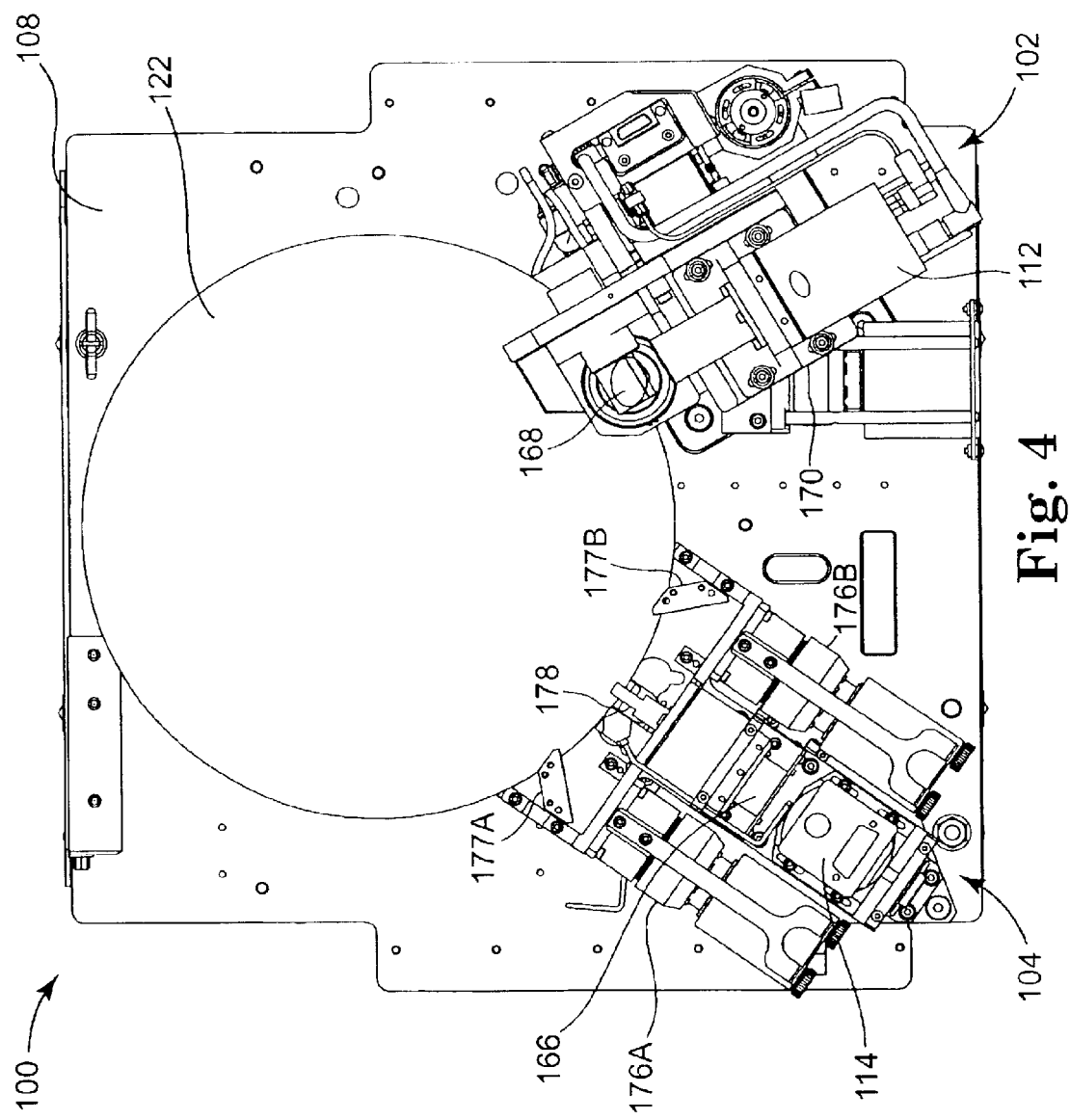
FIG. 4 is a top view illustrating one embodiment of the edge inspection system.
Figure 5:
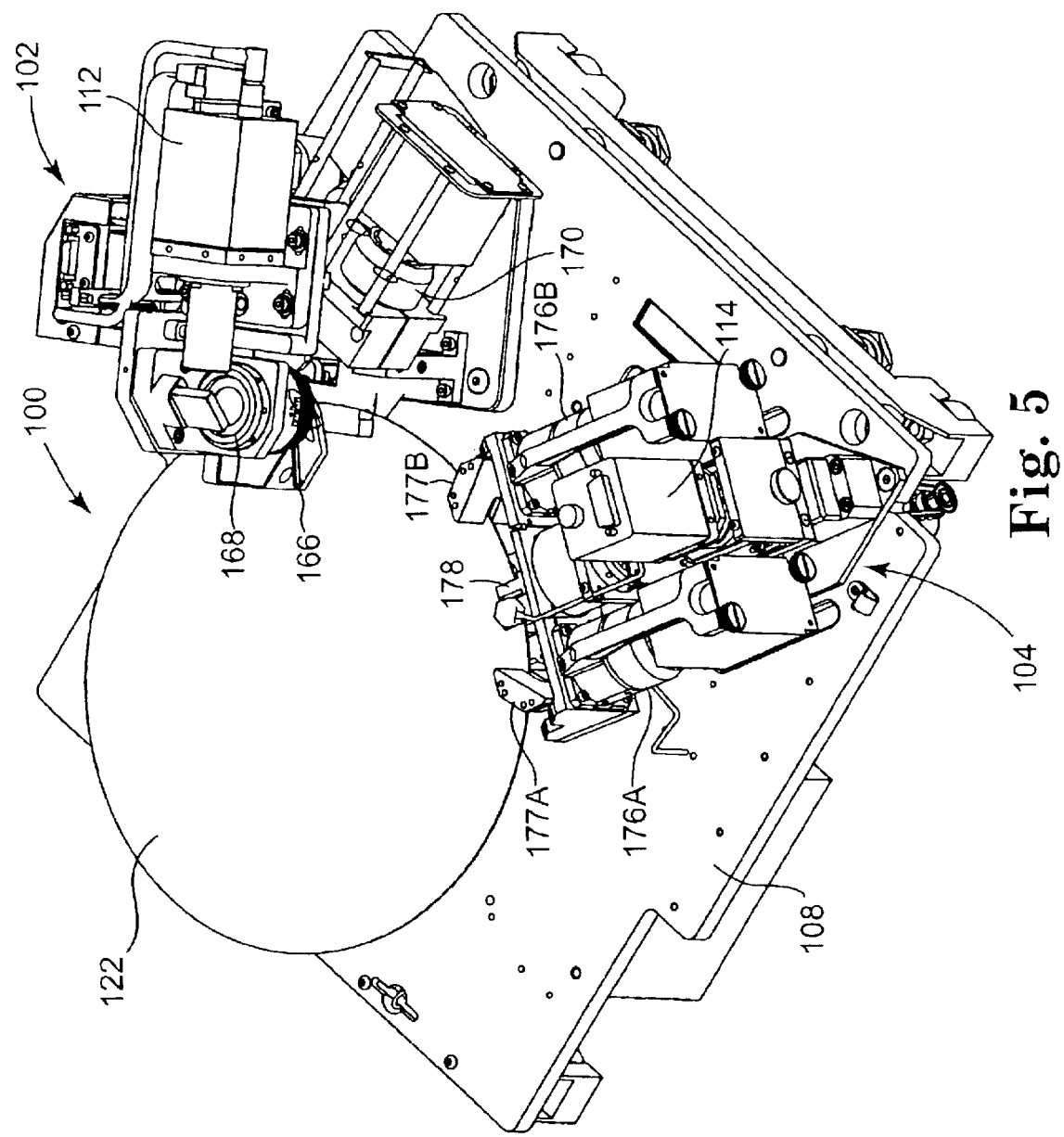
FIG. 5 is an angled perspective view illustrating one embodiment of the edge inspecting system.
Figure 6:
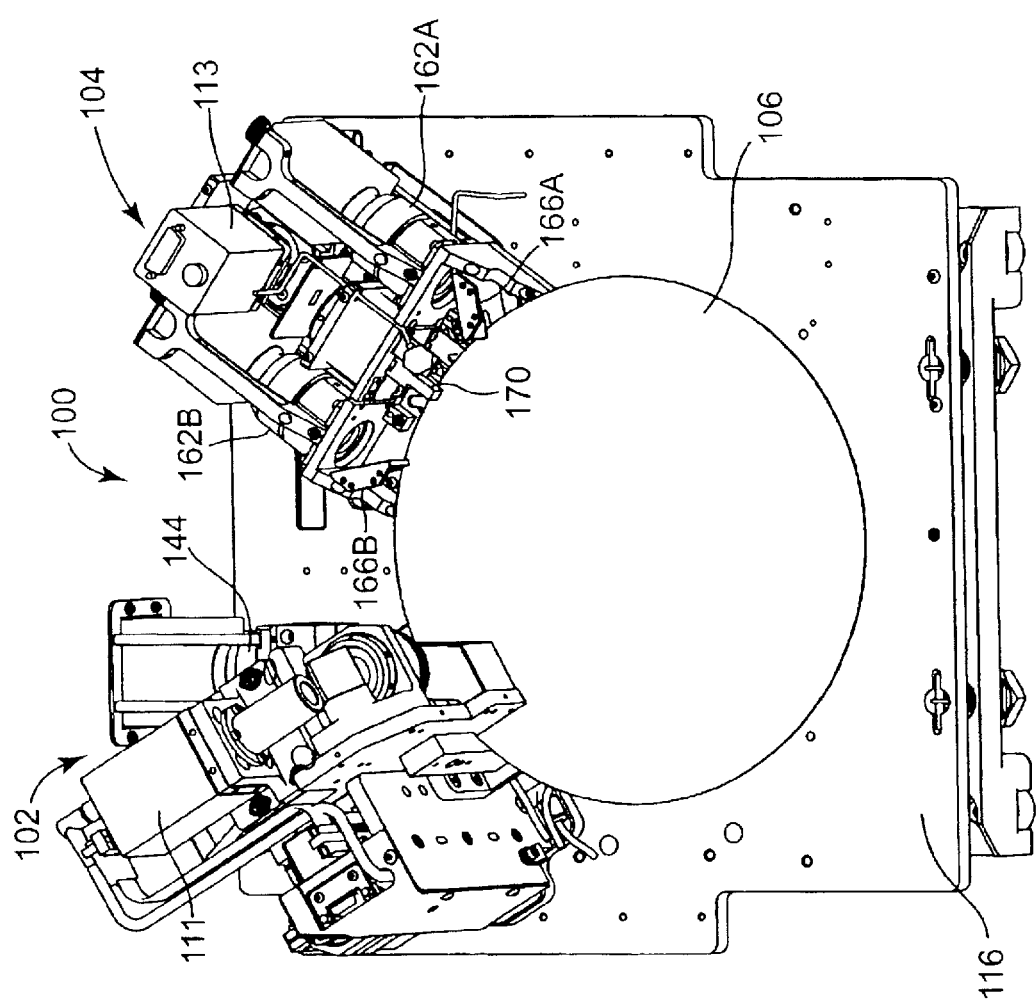
FIG. 6 is a front perspective view illustrating one embodiment of the edge inspection system.
Figure 7:
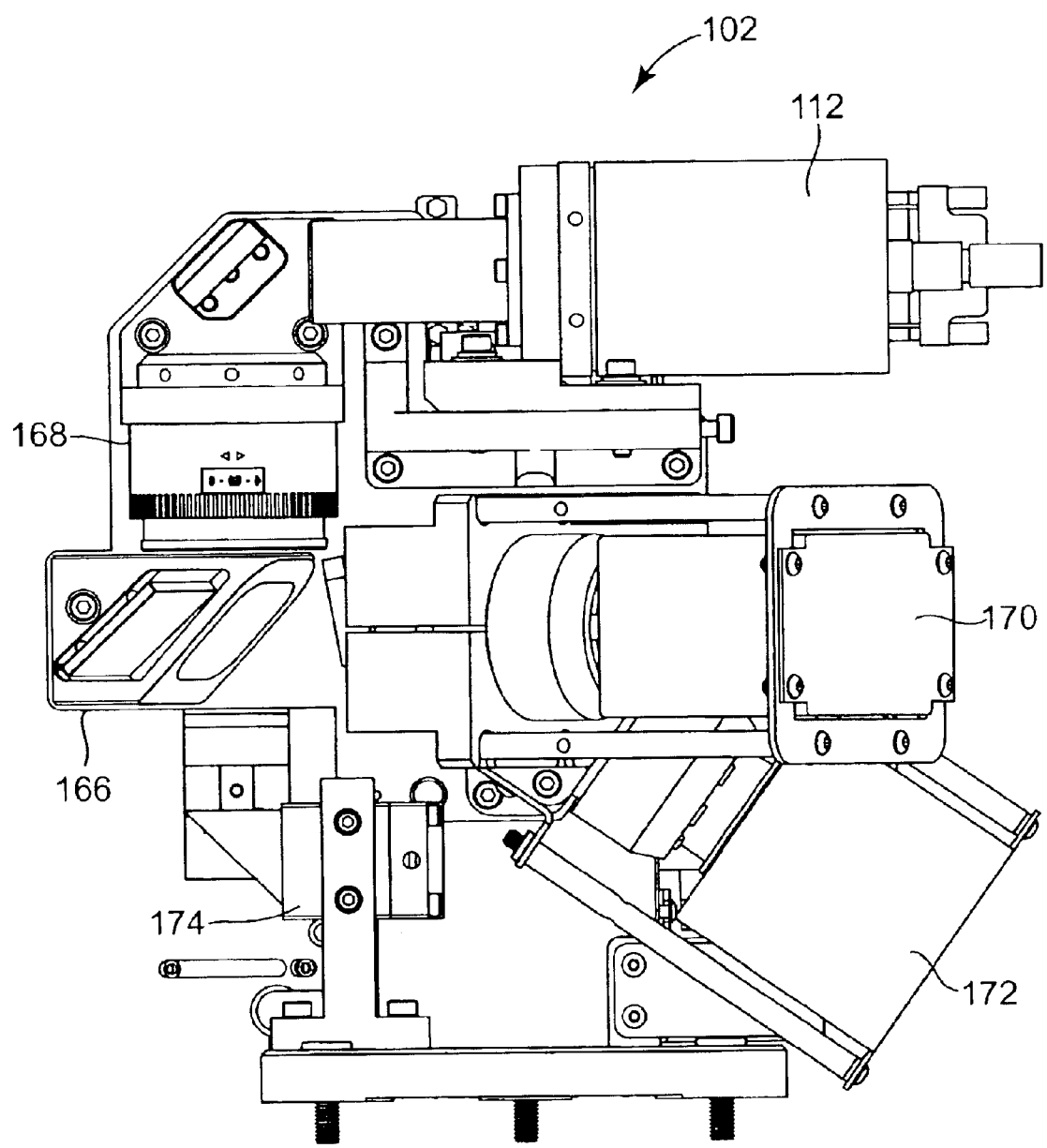
FIG. 7 is a side view illustrating one embodiment of an edge top sensor.

FIGS. 4-6 illustrate varying views of one embodiment of edge inspection system 100. FIG. 4 illustrates a top view, FIG. 5 illustrates an angled perspective view, and FIG. 6 illustrates a front perspective view of edge inspection system 100. FIG. 7 illustrates a side view of one embodiment of edge top sensor 102, and FIG. 8 illustrates a perspective view of one embodiment of edge normal sensor 104.

Edge top sensor 102 is an inspection sensor and, as illustrated in FIG. 7, includes edge top camera 112, a beamsplitter 166, optics 168, a brightfield light or strobe 170, a darkfield light or strobe 172, a backlight 174, and a servo motor and focus stage (not shown for clarity purposes). Edge top camera 112, in one embodiment, is a color camera with the following specifications, although other parameters may be used: 10×5 mm field of view (FOV), 5 μm resolution, and 360° continuous coverage of the wafer edge in both brightfield and darkfield modes.

Figure 8:
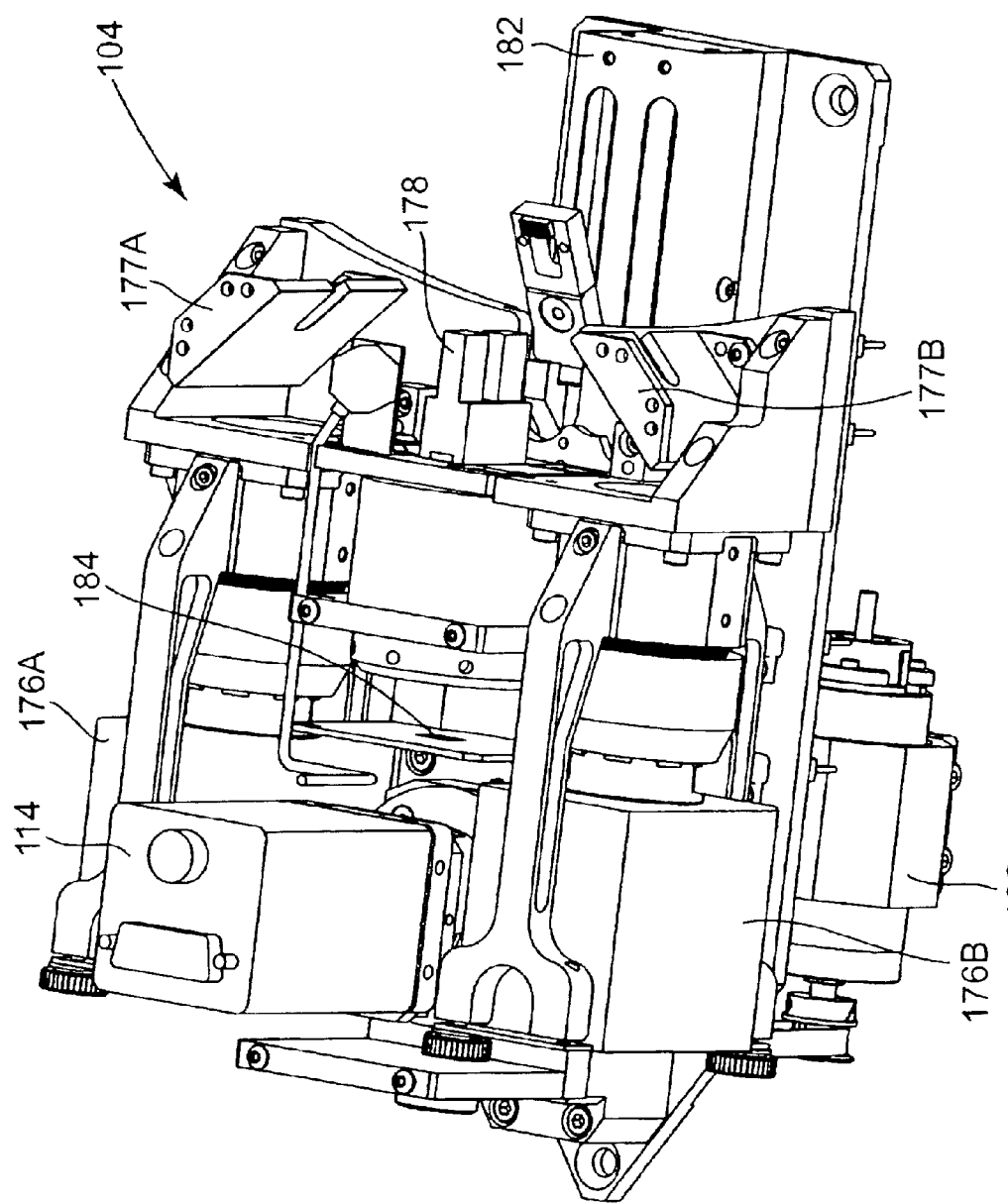
FIG. 8 is a perspective view illustrating one embodiment of an edge normal sensor.

Edge normal sensor 104 is an inspection sensor and, as illustrated in FIG. 8, includes edge normal camera 114 and one or more strobes, such as strobes 176A and 176B, and mirrors 177A and 177B. Edge normal camera 114, in one embodiment, is positioned so as to look at the thin profile of wafer 122. Camera 114, in one embodiment, is a single chip color camera with the following specifications, although other parameters may be used: 4×2 mm FOV, 4 μm resolution, and 360° continuous coverage of the wafer edge in mixed mode lighting. In one embodiment, the one or more strobes 176A and 176B are incident on wafer edge bevel 146 while simultaneously incident on diffuser 178 to provide mixed mode lighting.

Edge inspection system 100 of the present invention is used in one embodiment to inspect the edge of a substrate such as a semiconductor wafer. For example, edge inspection system 100 can inspect edge 124 of wafer 122. Edge inspection system 100 is a unique system that uses multiple cameras, such as cameras 112 and 114, with corresponding strobe lights, such as strobe lights 176A and 176B for edge normal camera 114, and brightfield light 170 and darkfield light 172 (FIG. 7) for edge top camera 112. Edge top camera 112 and edge normal camera 114 are used to acquire image data around the circumference of a substrate or wafer 122 for both the top of edge 124 of wafer 122 and wafer edge bevel 146, respectively. In one embodiment, edge normal camera 114 and edge top camera 112 have 4 μm and 51 μm image resolution, respectively, and special lighting diffusers to enable the detection of defects. One such diffuser 178 is illustrated attached to edge normal camera 114 in FIG. 4.

In one embodiment, edge inspection system 100 collects or captures image data for 100% of the circumference of wafer 122 for processing and analysis. In addition, according to one form of the invention, the images are in color for better defect classification. Further, strobe lights 176A and 176B enable greater depth-of-field for edge normal camera 114, enabling easier review of wafer edge bevel 146 by not having to focus on wafer edge bevel 146. Even more, edge top camera 112 captures two passes of data around the circumference of wafer 122. The first pass is brightfield data, while the second pass is darkfield data. This enables more reliable detection of EBR line 142 for resist removal metrology and the ability to better detect and classify particles and other contaminants as either surface particles or embedded particles. In one embodiment, all of the data from a single wafer is collected in less than approximately 10 seconds and processed in less than approximately 30 seconds.

In operation of edge top sensor 102, wafer 122 is spun by motor 116. In one embodiment, wafer 122 is spun two revolutions or most preferably slightly more than two full revolutions such as 2.1 revolutions or the like to provide a bit of overlap to assure that all data is collected. In the first revolution, the brightfield strobe 170 and backlight 174 are illuminated and images are gathered around the circumference of wafer 122. The images are passed to controller 106 where algorithms process the images to look for defects, wafer center, wafer edges, EBR lines, and the notch. Edge data of wafer 122 is fed to the motion control system (not shown for clarity purposes) of edge normal camera 114 in order to keep edge normal camera 114 in focus while edge normal camera 114 is inspecting edge 124 of wafer 122. In the second revolution, darkfield images are collected at the same positions on wafer 122 as the corresponding brightfield images.

The wafer edge data obtained by edge top camera 112 during the first revolution is used to focus edge normal camera 114 by controlling servo motor 180 to move sensor 104 on focus stage 182. In one embodiment, dual strobes 176A and 176B with diffuser 178 and a small aperture 184 enable 0.5 mm depth-of-field for edge normal camera 114. During the second revolution, the edge normal images are collected from 100% of the circumference of wafer 122. The images are passed to controller 106 where the algorithms process the images to look for defects. Furthermore, in one embodiment, edge normal camera 114 is a color camera, thus enabling better defect capture ability such as thin film variation, particles, delamination, residual resist, slurry ring, etc.

Edge inspection system 100 includes staging 130 that has support plate 120 thereon on which wafer 122 is loaded during operation. In one embodiment, staging 130 is a Continuous Rotate Stage including motor 116 and encoder 118. In one embodiment, encoder 118 is a 1.3 Million Counts/Rev encoder. In one form of the invention, stage 130 includes a vacuum to hold wafer 122 in place on support plate 120.

In one embodiment, edge inspection system 100 is packaged in an integrated metrology module of the type contemplated under draft Semiconductor Equipment and Materials (SEMI) standard 3377C for integrated metrology modules (IMM). In this embodiment, edge inspection system 100 attaches to a loadport using an interface such as a 300 mm BOLTS interface. In one embodiment, edge inspection system 100 is part of multiple inspection modules clustered about a single robot and controller, thereby reducing handling costs and inspection data flow costs. This novel multiple inspection module approach further allows more than one module of the same type to be attached to the cluster to improve throughput or add reliability.

Overall, edge inspection system 100 detects defects and variations along the edge 124 of wafer 122, such as particles, chips, cracks, delamination, copper-overflow, resist particles, embedded particles, etc. Detecting these types of defects enables either re-work, discontinuing processing, or process enhancement to achieve better yields. In one embodiment, edge inspection system 100 is very fast (in one embodiment over 100 wafers per hour), of a small form factor, low cost, robust, and offline review capable (preferably in color images).

In more detail, edge inspection system 100 performs various processes, including either or both EBR and edge of wafer (EEW) metrology measurement, chip and/or crack inspection, contamination and/or particles inspection, and delamination inspection using image processing techniques. The EBR and/or EEW metrology step involves analyzing the images to obtain the measurement from wafer edge normal 152 of wafer 122 to EBR line 142 of resist layer 140. The chip and/or crack inspection involves analyzing the images for chips and cracks evident along wafer edge normal 152, top bevel 150, and bottom bevel 154. The contamination and/or particles inspection involves analyzing the images for anomalies found on wafer edge bevel 146 or in edge exclusion region 144 of wafer 122. The delamination inspection involves analyzing the images for layer separation evident along wafer edge normal 152, top bevel 150, or bottom bevel 154.

As to performance, many external factors such as wafer type and conditions influence performance levels such as speed and accuracy. In one embodiment, however, edge inspection system 100 has the following EBR and/or EEW metrology performance characteristics: up to and including full 360° continuous measurements (selectable amounts less than this), 1° increments, 50 $\mu$m accuracy, and 10 $\mu$m repeatability. As to chips and cracks, 100 $\mu$m or greater accuracy is provided. As to contamination and particles, 5 $\mu$m resolution and full coverage edge top and edge normal is provided. As to overall performance, according to one form of the invention, edge inspection system 100 is capable of full color defect images, multiple revolutions per inspection, approximately 20 seconds per complete inspection using both edge top 102 and edge normal 104 sensors, approximately 12 seconds for wafer handling, and approximately 120 or more wafers per hour (WPH).

Figure 9:
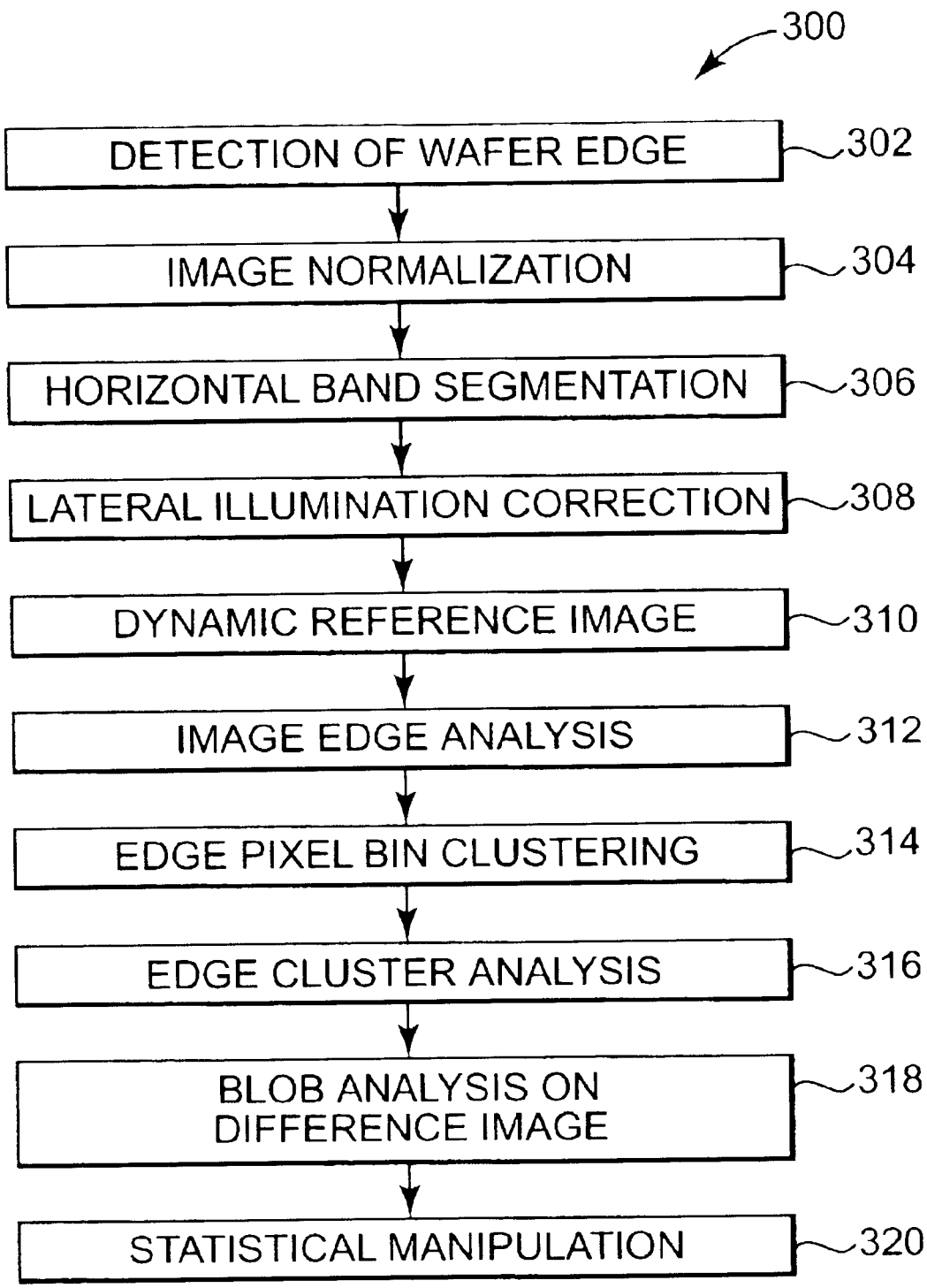
FIG. 9 is a flow diagram illustrating one embodiment of a method for inspecting a normal edge of a semiconductor wafer.

FIG. 9 is a flow diagram illustrating one embodiment of a method for inspecting a normal edge of a semi-conductor wafer, such as wafer edge normal 152 of wafer 122. The edge normal inspection method of the present invention maybe used on any of a number of edge inspection systems, such as edge inspection system 100 shown described with reference to FIGS. 1–8. In general, method 300, shown in FIG. 9, inspects wafer edge normal 152 and identifies defects due to delamination of thinfilms, chipping and cracking of the wafer, resist removal metrology, and particle detection that all cause yield issues in a modem fab. Method 300 includes the following steps: detection of the wafer edge (step 302), image normalization (step 304), horizontal band segmentation (step 306), lateral illumination correction (step 308), dynamic reference imaging (step 310), image edge analysis (step 312), edge pixel bin clustering (step 314), edge cluster analysis (step 316), blob analysis on difference image (step 318), and statistical manipulation (step 320). In one embodiment, the present method performs all essential image processing steps using the green channel. Red and blue channels are determined only for all defect areas to achieve color defect classification. In another embodiment, red and blue channel processing may also be included in all essential image processing steps.

Figure 10:
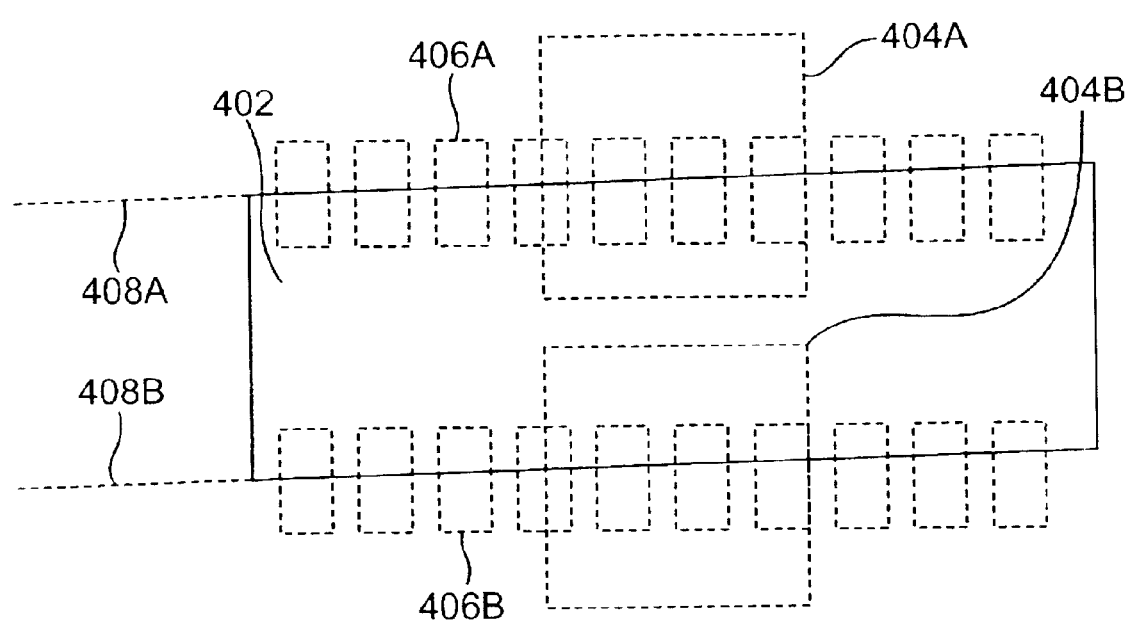
FIG. 10 is a partial side view illustrating wafer edge normal detection.

At 302, the detection of wafer edge 124 is accomplished and shown in greater detail in FIG. 10. Illustrated in FIG. 10 is wafer normal edge 402, coarse edge detections 404A and 404B, fine edge detections 406A and 406B, and least square fit lines 408A and 408B. A zero-crossing edge detector can be used to locate the top and bottom sides of the wafer foreground process area and is a three step process: first, top and bottom wafer side coarse detections 404A and 404B are centered at the middle of the image generate coarse detection. Second, fine edge detections 406A and 406B sample projections along the top and bottom wafer sides estimated in the preceding coarse detection. Third, least square fit lines 408A and 408B are used to compute parametric representations for the wafer top and bottom sides using edge sample positions generated during fine detection.

Figure 11A:
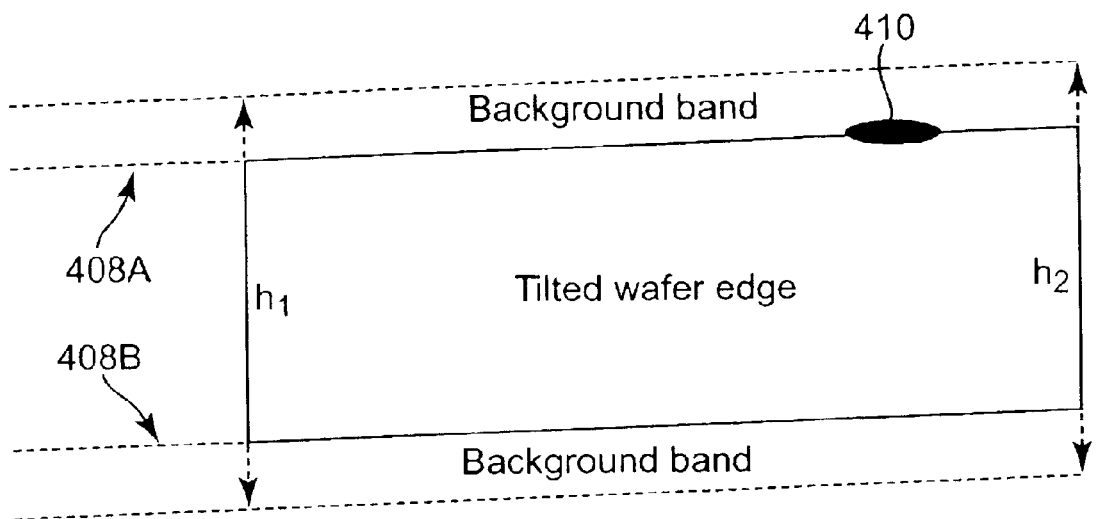
FIGS. 11A and 11B are partial side views illustrating a normal edge of a wafer.
Figure 11B:
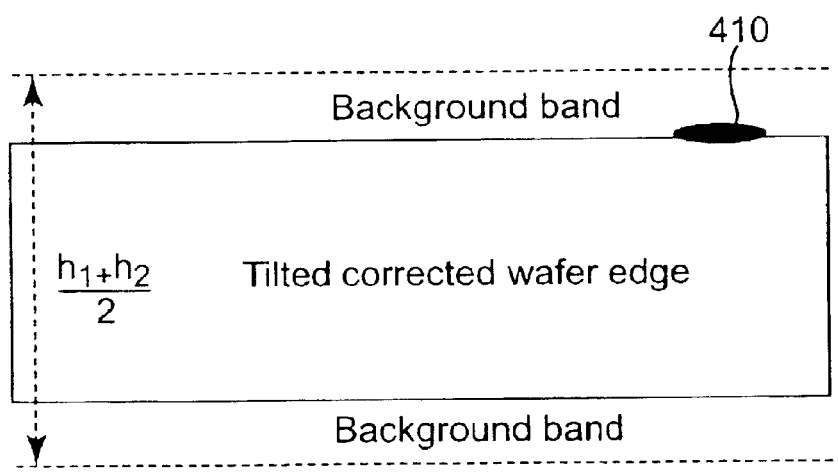

Due to human or robotic error, the original wafer in the test image is usually tilted, as shown in FIG. 11A. This complicates foreground pixel access for subsequent image processing. To alleviate this problem and thus reduces processing time, at 304, a new normalized scene image is generated as shown in FIG. 11B using least square fit line equations 408A and 408B for top and bottom sides (from step 302) to correct for wafer tilt. The normalized scene image is aligned such that the image is parallel to the horizontal axis of inspection system 100. The height of the wafer edge is determined by the equation $(h_1+h_2)/2$. In addition, wafer anamoly 410 is unaltered during the normalization process. In order to find anomalies just above or below the wafer edge normal view, the normalized scene image can also include predefined bands of background regions adjacent to the wafer foreground region as shown in FIG. 11B. The remaining processing steps are applied to the normalized scene image and not the original test image.

Figure 12:
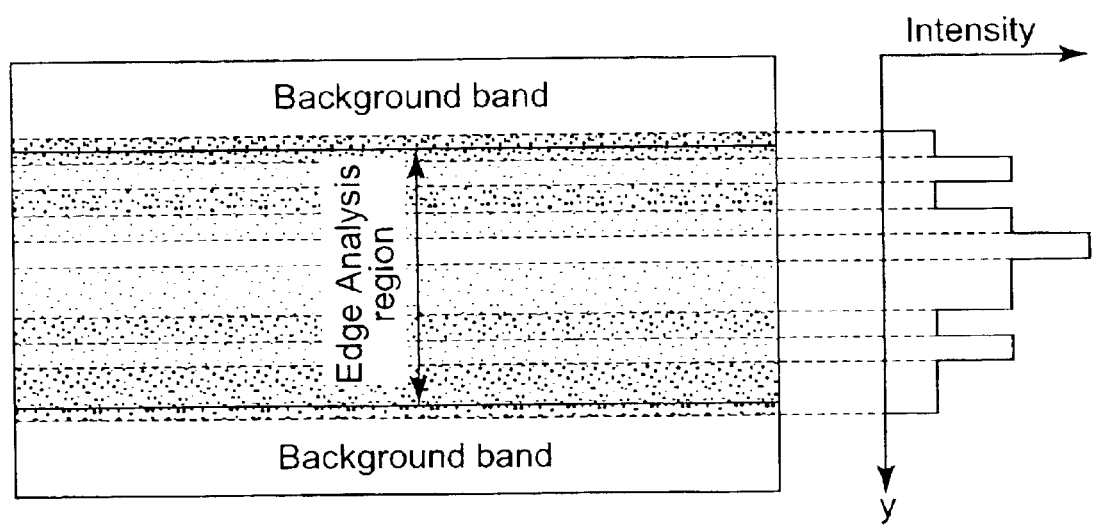
FIG. 12 is a diagram illustrating the intensity of various wafer normal edge bands.

At 306, the normalized scene image is segmented into horizontal bands of uniform (or near uniform) shades as shown in FIG. 12. Segmentation is accomplished by detecting fairly large intensity transitions in the vertical projection of mean pixel intensity on each scan line in the scene image.

The region inside the foreground region as well as two background bands immediately on top of and below the foreground region are analyzed. In one embodiment, each band should not be thinner than a minimum band thickness. In one embodiment and as shown in FIG. 12, both the top and bottom background bands have similar band thicknesses that are pre-determined. Foreground horizontal bands, however, are segmented by splitting up the region at the Y positions that correspond to local edge maximas (after canny-type edge filtering) in the horizontal projection of each scan line in the foreground local edge maxima above average edge strength.

Each horizontal band has a maximum Y position, a light variation correction and a high intensity error threshold. The high intensity error threshold is calculated during creation of the intensity different image for the process area. The threshold is the absolute intensity error value that separates the top pre-defined percentage (in one embodiment, the top one percent) of the highest intensity error pixels from remaining pixels with lower absolute intensity errors.

Figure 13A:
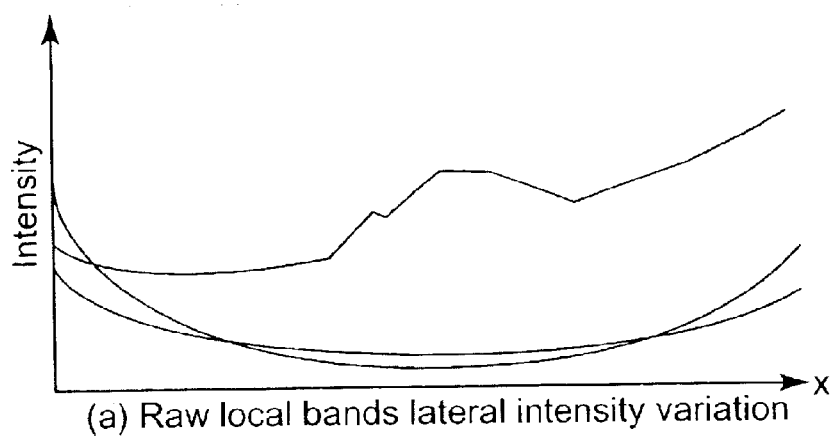
FIGS. 13A–13C are graphs illustrating intensities of various lateral bands of a normal edge of a wafer.
Figure 13B:
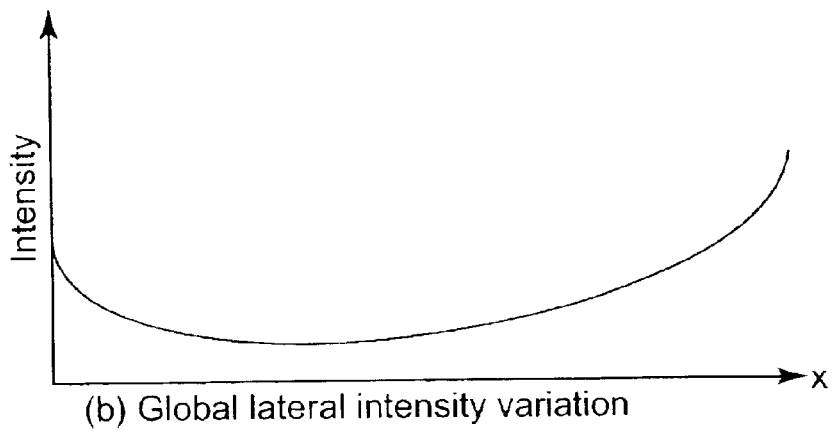
Figure 13C:
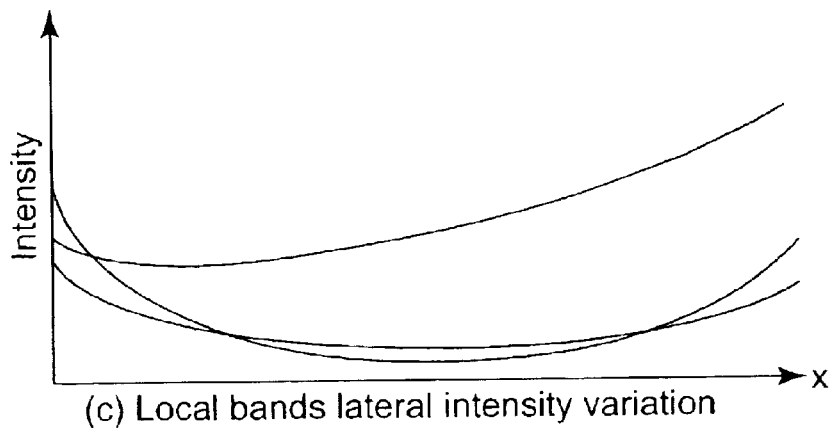

It is difficult to obtain uniform illumination across the image from left to right due to the wafer edge surface curvature and the existing opto-mechanical setup of the system. In most cases, this results in sometimes large intensity variations. These intensity variations can easily degrade inspection performance since it is non-trivial to distinguish between intensity variation representing actual defects and intensity variations representing non-uniform illumination variations. At 308, lateral illumination correction is accomplished and the undesirable effect of lighting variation across the image is reduced by subtracting the underlying local lateral illumination error for each segmented horizontal band. As shown in FIGS. 13A, 13B, and 13C, lateral intensity variations of a local band (FIG. 13C) is determined by combining information from the raw local bands lateral intensity variations (FIG. 13A) and the global lateral intensity variations (FIG. 13B).

More specifically, the local lateral illumination error for a horizontal band is determined in two steps. First, a local column intensity error vector is determined for each horizontal band. This local error vector contains the mean error for each column in a specific horizontal band. In other words, the local error vector comprises the difference between the mean intensity of each column and the overall mean intensity of the entire horizontal band. A global column error vector is also generated by averaging all the local column error vectors. Second, the local column error vector for each horizontal band is corrected to follow the general trend of the global column error vector while retaining most of its local column variation. This step is needed to separate intensity variations caused by real defects from intensity variations caused by illumination error.

At 310, the vertical projection intensity shown in FIG. 12 and the local band lateral intensity variation shown in FIG. 13C are combined to create a dynamic reference image or model of a defect-free wafer image. Later in the process or method, this model will be utilized to find defects in wafer edge using blob analysis (step 318).

In many wafer-fabrication defect cases, such as defects due to peel-off, the defect is not a distinguishing blob in contrast with adjacent properly fabricated wafer sections. Instead, fabrication defects can have intensities that blend well with the surface intensity except for small regions of sharp intensity variations within the defect area and around the perimeter of defect. At 312, image edge analysis is performed. High frequency features or edge pixels for each horizontal band are enhanced by determining the local intensity variation for each pixel compared to a number of neighboring pixels. Heuristics are deployed to remove relatively small edge pixel clusters and to eradicate inherent intensity variations between horizontal bands in the vertical direction.

Edge pixels usually appear as small separated clusters. At 314, edge pixel bin clustering includes combining or connecting nearby edge clusters so that the system can associate a group of edge clusters to a single defect area. Each horizontal band is divided into several 50 percent overlapping vertical columns called bins. All edge pixels within a bin are considered as a single entity. Adjacent overlapping bins share edge pixels.

Two techniques are used to identify defects on the wafer: edge cluster analysis and blob analysis. At 316, in one embodiment, edge cluster analysis scans the edge cluster bins for continuous sets of non-empty bins with significantly high edge pixel counts such as greater than 120% of the average edge pixel count. In one embodiment, edge cluster analysis scans the edge cluster bins for continuous sets of non-empty bins with edge pixel counts between 120% and 150% of the average edge pixel count. If found, a single surface variation defect is associated to the bounding rectangular region of a continuous set of prominent non-empty edge pixel bins.

At 318, in one embodiment, blob analysis is applied to the difference image between the normalized scene image and the dynamic model reference image to detect blobs with high pixel errors such as greater than 180% of the average pixel error. In one embodiment, blob analysis is applied to the difference image between the normalized scene image and the dynamic model reference image to detect blobs with pixel errors between 180% and 200% of the average pixel error. A simple auto-thresholding technique is used to determine the minimum error threshold that will classify a pixel as defect. Additionally, the blob analysis also checks for edge pixel counts and perimeter contrast for each error pixel blob. This will help to reduce overkill caused by lighting variation as discussed earlier.

In addition to image processing techniques applied to each image frame to find potential wafer defects, at 320 a statistical model of defect and imaging attributes for horizontal bands along the wafer edge across all image frames captured for the wafer is determined or constructed. For example, the roughness and intensity measurements of fine resolution horizontal band regions in the image are maintained. After inspection of all the image frames for a wafer, fine band statistical data are dynamically combined to compare with the defect and image properties of horizontal bands segmented for each image frame. If a particular defect is a result of image properties for horizontal bands that are consistent for all image frames, the defect can be removed as potential overkill. One example of potential overkill includes surface variation defects found within a set of horizontal bands with consistently high roughness measurement for all the image frames. The surface variation defects will be removed because these defects are most likely inherent properties of an unpolished wafer region. Likewise, the statistical data can be used to identify potential escapes. For example, a set of horizontal bands in an image frame may be much brighter or darker than similar regions in other image frames. These horizontal bands will be marked as defects because they are most probably large peel-off regions spanning over more than one image frame.

Edge inspection system 100 which incorporates edge normal detection method 300 provides inspection of a normal edge of a wafer to identify defects therealong. Quality control during the fabrication process is greatly heightened.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. An edge inspection method for detecting defects on a wafer edge normal surface, the method comprising:
   acquiring a set of digital images capturing a circumference of the wafer;
   determining an edge of the wafer about the circumference of the wafer;
   segmenting each digital image into a plurality of horizontal bands;
   combine adjacent edge clusters about the circumference of the wafer into edge pixel bins;
   analyze the edge pixel bins via edge cluster analysis to identify defects; and
   analyze the edge pixel bins via blob analysis to identify defects.

2. The method of claim 1 and further comprising:
   normalizing the set of digital images; and
   segmenting each normalized digital image into a plurality of horizontal bands.

3. The method of claim 1 and further comprising:
   performing lateral illumination correction on each of the plurality of segmented horizontal bands.

4. The method of claim 3 wherein performing lateral illumination correction on each of the plurality of segmented horizontal bands further comprises:
   subtracting an underlying local lateral illumination error for each of the plurality of segmented horizontal bands.

5. The method of claim 1 and further comprising:
   creating a dynamic reference image of a defect-free wafer image.

6. The method of claim 5 wherein creating a dynamic reference image of a defect-free wafer image further comprises:
   combining a vertical projection intensity and a local band lateral intensity variation, thereby creating the dynamic reference image.

7. The method of claim 1 and further comprising:
   performing image edge analysis on the plurality of segmented horizontal bands.

8. The method of claim 1 wherein segmenting each digital image into a plurality of horizontal bands further comprises:
   detecting intensity transitions in a vertical projection of mean pixel intensity on each scan line in the digital image.

9. The method of claim 1 wherein the step of combining adjacent edge clusters into edge pixel bins further comprises:
   dividing each horizontal band into several overlapping vertical bins.

10. The method of claim 1 wherein analyzing the edge pixel bins via edge cluster analysis further comprises:
    scanning the edge pixel bins for continuous sets of non-empty bins having an edge pixel count greater than 120% of an average edge pixel count; and
    associating a single surface variation defect with a bound rectangular region about the edge cluster bin having an edge pixel count greater than 120%.

11. The method of claim 1 wherein the step of analyzing the edge pixel bins via blob analysis further comprises:
    detecting blobs having pixel errors greater than 180% of the average pixel error.

12. The method of claim 1 and further comprising:
    constructing a statistical model of defects for each of the plurality of segmented horizontal bands.

13. An edge inspection method for detecting defects on a wafer edge normal surface, the method comprising:
    acquiring a set of digital images capturing a circumference of the wafer;
    determining an edge of the wafer about the circumference of the wafer;
    segmenting each digital image into a plurality of horizontal bands;
    combine adjacent edge clusters about the circumference of the wafer into edge pixel bins; and
    analyze the edge pixel bins via edge cluster analysis to identify defects.

14. The method of claim 13 and further comprising:
    normalizing the set of digital images; and
    segmenting each normalized digital image into a plurality of horizontal bands.

15. The method of claim 13 and further comprising:
    performing lateral illumination correction on each of the plurality of segmented horizontal bands.

16. The method of claim 15 wherein performing lateral illumination correction on each of the plurality of segmented horizontal bands further comprises:
    subtracting an underlying local lateral illumination error for each of the plurality of segmented horizontal bands.

17. The method of claim 13 and further comprising:
    creating a dynamic reference image of a defect-free wafer image.

18. The method of claim 17 wherein creating a dynamic reference image of a defect-free wafer image further comprises:
    combining a vertical projection intensity and a local band lateral intensity variation, thereby creating the dynamic reference image.

19. The method of claim 13 and further comprising:
    performing image edge analysis on the plurality of segmented horizontal bands.

20. The method of claim 13 wherein segmenting each digital image into a plurality of horizontal bands further comprises:
    detecting intensity transitions in a vertical projection of mean pixel intensity on each scan line in the digital image.

21. The method of claim 13 wherein the step of combining adjacent edge clusters into edge pixel bins further comprises:
    dividing each horizontal band into several overlapping vertical bins.

22. The method of claim 13 wherein analyzing the edge pixel bins via edge cluster analysis further comprises:
- scanning the edge pixel bins for continuous sets of non-empty bins having an edge pixel count greater than 120% of an average edge pixel count; and
- associating a single surface variation defect with a bound rectangular region about the edge cluster bin having an edge pixel count greater than 120%.

23. The method of claim 13 and further comprising:
- constructing a statistical model of defects for each of the plurality of segmented horizontal bands.

24. An edge inspection method for detecting defects on a wafer edge normal surface, the method comprising:
- acquiring a set of digital images capturing a circumference of the wafer;
- determining an edge of the wafer about the circumference of the wafer;
- segmenting each digital image into a plurality of horizontal bands;
- combine adjacent edge clusters about the circumference of the wafer into edge pixel bins; and
- analyze the edge pixel bins via blob analysis to identify defects.

25. The method of claim 24 and further comprising:
- normalizing the set of digital images; and
- segmenting each normalized digital image into a plurality of horizontal bands.

26. The method of claim 24 and further comprising:
- performing lateral illumination correction on each of the plurality of segmented horizontal bands.

27. The method of claim 26 wherein performing lateral illumination correction on each of the plurality of segmented horizontal bands further comprises:
- subtracting an underlying local lateral illumination error for each of the plurality of segmented horizontal bands.

28. The method of claim 24 and further comprising:
- creating a dynamic reference image of a defect-free wafer image.

29. The method of claim 28 wherein creating a dynamic reference image of a defect-free wafer image further comprises:
- combining a vertical projection intensity and a local band lateral intensity variation, thereby creating the dynamic reference image.

30. The method of claim 24 and further comprising:
- performing image edge analysis of a plurality of segmented horizontal bands.

31. The method of claim 24 wherein segmenting each digital image into a plurality of horizontal bands further comprises:
- detecting intensity transitions in a vertical projection of mean pixel intensity on each scan line in the digital image.

32. The method of claim 24 wherein the step of combining adjacent edge clusters into edge pixel bins further comprises:
- dividing each horizontal band into several overlapping vertical bins.

* * * * *